United States Patent
Sun et al.

(10) Patent No.: US 10,654,781 B2
(45) Date of Patent: May 19, 2020

(54) METHOD OF CATALYTIC CONVERSION OF CARBOHYDRATES TO LOW-CARBON DIOLS BY USING ALLOY CATALYSTS

(71) Applicant: DALIAN INSTITUTE OF CHEMICAL PHYSICS, CHINESE ACADEMY OF SCIENCES, Dalian, Liaoning (CN)

(72) Inventors: Ruiyan Sun, Liaoning (CN); Mingyuan Zheng, Liaoning (CN); Tao Zhang, Liaoning (CN); Jifeng Pang, Liaoning (CN); Yu Jiang, Liaoning (CN); Aiqin Wang, Liaoning (CN); Xiaodong Wang, Liaoning (CN)

(73) Assignee: DALIAN INSTITUTE OF CHEMICAL PHYSICS, CHINESE ACADEMY OF SCIENCES, Dalian, Liaoning (CN)

(*) Notice: Subject to any disclaimer, the term of this patent is extended or adjusted under 35 U.S.C. 154(b) by 0 days.

(21) Appl. No.: 15/735,190

(22) PCT Filed: Nov. 26, 2015

(86) PCT No.: PCT/CN2015/095590
§ 371 (c)(1),
(2) Date: Dec. 10, 2017

(87) PCT Pub. No.: WO2017/079999
PCT Pub. Date: May 18, 2017

(65) Prior Publication Data
US 2018/0178201 A1 Jun. 28, 2018

(30) Foreign Application Priority Data
Nov. 12, 2015 (CN) .......................... 2015 1 0770769

(51) Int. Cl.
| | |
|---|---|
| B01J 23/89 | (2006.01) |
| B01J 35/00 | (2006.01) |
| B01J 37/02 | (2006.01) |
| B01J 23/62 | (2006.01) |
| B01J 33/00 | (2006.01) |
| B01J 25/02 | (2006.01) |
| B01J 37/18 | (2006.01) |
| B01J 23/835 | (2006.01) |
| C07C 29/132 | (2006.01) |

(52) U.S. Cl.
CPC .......... *C07C 29/132* (2013.01); *B01J 23/626* (2013.01); *B01J 23/835* (2013.01); *B01J 23/892* (2013.01); *B01J 23/8966* (2013.01); *B01J 25/02* (2013.01); *B01J 33/00* (2013.01); *B01J 35/002* (2013.01); *B01J 37/0201* (2013.01); *B01J 37/0236* (2013.01); *B01J 37/18* (2013.01); *Y02P 20/52* (2015.11)

(58) Field of Classification Search
None
See application file for complete search history.

(56) References Cited

U.S. PATENT DOCUMENTS

| | | | |
|---|---|---|---|
| 8,710,281 B2* | 4/2014 | Nagaki ................. | B01J 21/066 568/903 |
| 10,464,870 B2* | 11/2019 | Liu ....................... | B01J 23/8885 |
| 2012/0323051 A1* | 12/2012 | Powell ................... | C10G 3/00 568/913 |
| 2013/0281741 A1* | 10/2013 | Chambon .............. | C07C 29/132 568/386 |
| 2014/0005444 A1* | 1/2014 | Komplin ............... | C07C 29/132 568/861 |

FOREIGN PATENT DOCUMENTS

| | | |
|---|---|---|
| CN | 1463960 A | 12/2003 |
| CN | 101199930 A | 6/2008 |

(Continued)

OTHER PUBLICATIONS

Xiaoming Cui, "The development of ethylene glycol production technology home and abroad", Chemical Industry, 2007, 25, (4), 15-21 (English Abstract translation on p. 21).

Na Ji et al., "Direct catalytic conversion of cellulose into ethylene glycol using nickel-promoted tungsten carbide catalysts", Angew. Chem. Int. Ed. 2008, 47, 8510-8513.

Ming-Yuan Zheng et al., "Transition metal-tungsten bimetallic catalysts for the conversion of cellulose into ethylene glycol", ChemSusChem 2010, vol. 3, 63-66.

(Continued)

*Primary Examiner* — Rosalynd A Keys
(74) *Attorney, Agent, or Firm* — Novick, Kim & Lee, PLLC; Allen Xue

(57) ABSTRACT

This invention provides a method for catalytic conversion of carbohydrates to low-carbon diols using alloy catalysts. In the process, carbohydrates as the feedstock are subjected to one-step catalytic conversion to realize the highly efficient and selective production of ethylene glycol etc. under hydrothermal conditions, with an alloy catalyst composed of tin, and a transition metal such as iron, cobalt, nickel, rhodium, ruthenium, palladium, iridium, platinum and copper, or a mixture thereof. The reaction is carried out in water at a temperature range of 120-300° C., with a hydrogen pressure range of 1-13 MPa. Compared with the present petroleum based synthesis technology of ethylene glycol, the method in this invention possesses advantages of using renewable feedstock, high atom economy and environmental friendly. Besides, compared with other technologies using biomass as feedstock to produce ethylene glycol, the alloy catalyst in this invention possesses the advantages of few leaching amount, good hydrothermal stability and easy to recycle.

19 Claims, 1 Drawing Sheet

(56) References Cited

FOREIGN PATENT DOCUMENTS

| | | |
|---|---|---|
| CN | 101704710 A | 5/2010 |
| CN | 102190562 A | 9/2011 |
| CN | 101723802 B | 6/2013 |
| CN | 104119203 A | 10/2014 |
| CN | 104119207 A | 10/2014 |
| CN | 102675045 B | 4/2015 |
| CN | 104710277 A | 6/2015 |
| JP | 2013060379 A | 4/2013 |

OTHER PUBLICATIONS

Jiejing Chen et al., "NiSn/C Catalyst for Hydrogenolysis of Sugar Alcohol Mixture to Lower Diols", Petrochemical Technology, 2014, vol. 43, No. 7, pp. 816-820.

* cited by examiner

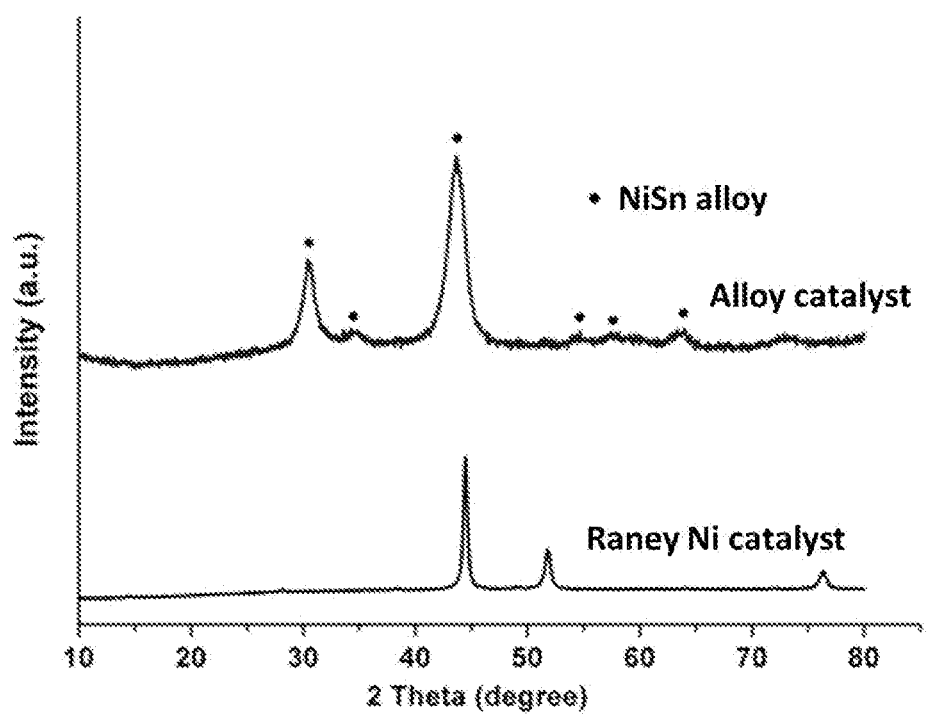

METHOD OF CATALYTIC CONVERSION OF CARBOHYDRATES TO LOW-CARBON DIOLS BY USING ALLOY CATALYSTS

FIELD OF THE INVENTION

The invention relates to a method for catalytic conversion of carbohydrates to low-carbon diols using alloy catalysts, and more particularly to a method for catalytically producing ethylene glycol from carbohydrates under hydrothermal conditions.

DESCRIPTION OF THE RELATED ART

Low-carbon diols, especially for ethylene glycol is important energy liquid fuels, and also important feedstock for the synthesis of polyesters, such as polyethylene terephthalate (PET) and polyethylene naphthalate (PEN). Ethylene glycol is also a versatile organic chemical feedstock used as anti-freezing agent, lubricant, plasticizer, surfactant and etc.

At present, the feedstock of industrial manufacture of ethylene glycol is the petroleum derived ethylene, which is epoxidized to ethylene oxide followed by hydration to ethylene glycol (Literature 1: Xiaoming Cui, The development of ethylene glycol production technology home and abroad, Chemical Industry, 2007, 25, (4), 15-21. Literature 2: Process for preparing ethanediol by catalyzing epoxyethane hydration, Patent No. CN1463960-A; CN1204103-C). The production technology of ethylene glycol depends on the non-renewable petroleum resources, and the manufacturing process includes selective oxidation or epoxidation steps, which makes the technology difficult, low efficiency, lots of by products, high energy consumption and serious pollution.

Using renewable biomass to produce ethylene glycol could reduce the dependence on fossil energy resources, and contributes to achieving environmentally benign and sustainable economy. Carbohydrates such as cellulose are the most abundant renewable resources in nature, and the cost of utilizing carbohydrates is very low. Using cellulosic carbohydrates to produce ethylene glycol not only provides a new synthesis route of ethylene glycol to realize the production of high valued chemicals from cheap carbohydrate, but also has no effect on the food safety of human beings because of the inedibility of cellulosic carbohydrates.

Now, ethylene glycol can be obtained by catalytic hydrogenation of cellulose under hydrothermal conditions (Literature 1: Direct catalytic conversion of cellulose into ethylene glycol using nickel-promoted tungsten carbide catalysts, Angew. Chem. Int. Ed. 2008, 47, 8510-8513; Literature 2: Transition metal-tungsten bimetallic catalysts for the conversion of cellulose into ethylene glycol, ChemSusChem 2010, 3, 63-66; Literature 3: CN 102190562 A, Method for producing ethylene glycol form carbohydrate compounds). These methods employ tungsten based catalysts and hydrogenation catalysts as composite catalysts for cellulose conversion, and 60-75% yield of ethylene glycol can be obtained.

Similarly, xylose which is hydrolyzed from the corncob can also be converted to ethylene glycol, propylene glycol and glycerol by catalytic hydrogenolysis (Literature 4: CN101704710A Preparing glycol, propanediol and glycerine involves converting corncob catalytically and hydrolyzing corncob by acid catalysis to prepare xylose-water solution). The overall selectivity of ethylene glycol and propylene glycol can reach 30%.

This invention provides a method for one-step conversion of carbohydrates to low-carbon diols using alloy catalysts. In the process, carbohydrates as the feedstock are subjected to catalytic conversion to realize the highly efficient and selective production of ethylene glycol etc. The method in this invention possesses the advantages of easy operation and low cost. Besides, the alloy catalysts provided by this method possess advantages of few leaching amount, good hydrothermal stability and easy to recycle.

SUMMARY OF THE INVENTION

The purpose of this invention is to provide a method for fast and highly efficient conversion of carbohydrates to low-carbon diols. The low-carbon diols are ethylene glycol or 1,2-propylene glycol, or a mixture thereof. Compared to the traditional method of producing ethylene glycol, the method in this invention possesses the advantages of easy operation and low cost. Besides, the alloy catalysts provided by this method possess advantages of few leaching amount, good hydrothermal stability and easy to recycle.

To achieve the above purpose, the technical solution of this invention is as follows:

Carbohydrates are used as the feedstock subjected to catalytic hydrogenation in high pressure reactor in water. The alloy catalyst is synthesized from at least two kinds of metal precursors;

The alloy catalyst is composed of tin and a transition metal selected from iron, cobalt, rhodium, ruthenium, palladium, iridium, platinum and copper, or a mixture thereof; the weight ratio between tin and other metals is in the range of 0.01-100.

Or, the alloy catalyst is composed of the precursors of tin and other metals before use; the precursors of tin are selected from metallic tin or tin compounds, or a mixture thereof; the precursors of other metals are selected from metallic iron, cobalt, rhodium, ruthenium, palladium, iridium, platinum and copper, or iron, cobalt, rhodium, ruthenium, palladium, iridium, platinum and copper compounds, or a mixture thereof; the alloy is in situ formed from tin and other metals and the weight ratio between tin and other metals is in the range of 0.01-100.

Or, the alloy catalyst was skeletal catalyst composed of metallic nickel and tin alloy.

The reaction is conducted in sealed high pressure reactor, continuous high pressure reactor or semi continuous high pressure reactor; the hydrogen is filled in the reactor before reaction; the reaction is conducted at temperatures higher than 120° C.; the reaction time is no less than 5 minutes or liquid hourly space velocity is not more than 20 h$^{-1}$.

The weight concentration of alloy catalyst in the reaction system is between 0.1% and 50%.

The hydrogen is filled in the reactor before reaction; the initial hydrogen pressure at room temperature is particularly between 1 and 12 MPa; the reaction temperature is higher than 120° C. and the upper limit of temperature is the highest temperature that the thermal decomposition of product do not occur.

The reaction temperature is particularly between 200 and 280° C.; the initial hydrogen pressure at room temperature is particularly between 3 and 7 MPa; with regard to the sealed high pressure reactor, the reaction time is between 0.5 and 5 h; with regard to the continuous high pressure reactor or semi continuous high pressure reactor, the liquid hourly space velocity is between 0.1 and 50 h$^{-1}$; the liquid hourly space velocity represents the ratio of the dry mass of feedstock into the reactor hourly to the mass of catalyst in the reactor. The operating mode of semi continuous high pressure reactor: aqueous solution of feedstock is pumped into the reactor under high temperature and high pressure; after completing the injection, keep the temperature and pressure for a while and then cool down the reactor to remove the product.

The alloy catalyst is a non-supported catalyst; the alloy catalyst is a skeletal metal catalyst, in which the metals of alloy compose the skeleton of catalyst; the preferred skeletal catalyst is composed of nickel-tin alloy; the weight ratio between tin and other metals is in the range of 0.1-10; the weight concentration of alloy catalyst in the reaction system is between 1% and 30%.

The weight ratio between tin and other metals in the skeleton alloy catalyst is in the range of 0.5-2; the weight concentration of alloy catalyst in the reaction system is between 2% and 20%.

The alloy catalyst is a supported catalyst; metallic tin and other metals including iron, cobalt, rhodium, ruthenium, palladium, iridium, platinum and copper, or a mixture thereof are supported on a carrier; the carrier is selected from activated carbon, alumina, silica, silicon carbide, zirconia, zinc oxide and titanium dioxide, or a mixture thereof; the weight concentration of alloy in the supported catalyst is between 0.01% and 50 wt %; the weight ratio between tin and other metals in the supported catalyst is in the range of 0.1-10.

The weight concentration of alloy in the supported catalyst is between 1% and 35 wt %; the weight ratio between tin and other metals in the supported catalyst is in the range of 0.5-2.

Metallic or compounds of transition metals including iron, cobalt, rhodium, ruthenium, palladium, iridium, platinum and copper, or a mixture thereof are supported on a carrier; the carrier is selected from metallic tin or tin compounds, or a mixture thereof; the weight concentration of transition metals in the catalyst is between 0.01% and 50 wt %.

Or, metallic tin or tin compounds, or a mixture thereof are supported on a carrier; the carrier is selected from metallic or compounds of transition metals including iron, cobalt, rhodium, ruthenium, palladium, iridium, platinum and copper, or a mixture thereof; the weight concentration of tin in the catalyst is between 0.01% and 50 wt %.

The masses of water and feedstock put into the reactor should ensure that the status of the whole material in the reactor under reaction condition is partially or completely is liquid.

Carbohydrate is selected from cellulose, starch, hemicellulose, jerusalem artichoke, saccharose, glucose, mannose, fructose, levulan, xylose, arabinose, xylooligosaccharide, erythrose and chitosan, or a mixture thereof.

Metallic tin or tin compounds including metallic tin, stannous fluoride, stannous fluoride, stannous bromide, stannous iodide, stannic fluoride, stannic chloride, stannic bromide, stannic iodide, stannic hydroxide, stannous hydroxide, stannous oxide, stannic oxide, stannous mono-sulphate, stannic acetate, stannous oxalate, sodium stannate, potassium stannate, calcium stannate, tin phosphide and stannous pyrophosphate, or a mixture thereof.

Metallic or compounds of transition metals including metallic iron, metallic cobalt, metallic rhodium, metallic ruthenium, metallic palladium, metallic iridium, metallic platinum, metallic copper, skeletal iron (Raney iron), skeletal cobalt (Raney cobalt), skeletal copper (Raney copper), ferric nitrate, cobalt nitrate, ruthenium nitrosyl nitrate, rhodium nitrate, palladium nitrate, iridium nitrate, platinum nitrate, copper nitrate, ferric chloride, cobalt chloride, ruthenium chloride, rhodium chloride, palladium chloride, iridium chloride, platinum chloride, copper chloride, ferric oxide, ferroferric oxide, ferrous oxide, iron sulfate, cobalt (II) oxide, cobalt sesquioxide, cobaltosic oxide, cobaltous sulfate, nickel sulfate, copper oxide and copper sulfate, or a mixture thereof.

ADVANTAGES OF THE INVENTION ARE SUMMARIZED AS BELOW

1. The feedstock adopted in the invention is cellulosic carbohydrates which are cheap and abundant. Compared to the ethylene which is used as the feedstock in the industrial manufacture of ethylene glycol, using renewable cellulosic carbohydrates as feedstock is important for the sustainable development, the utilization of waste products and farmers' income growth.
2. The structure of alloy catalysts in this invention is stable, and the leaching amount is quite low.
3. The alloy catalysts present neutral or slight basicity in use, so the corrosion to the equipment is weak when long time use of alloy catalyst, which will save the investment of equipment.
4. The heterogeneous alloy catalysts are easy to separate from solution and stable in the cycle experiment.

DESCRIPTION OF THE DRAWING

FIG. 1 XRD pattern of the skeletal NiSn alloy catalyst prepared by hydrothermal treatment

DETAILED DESCRIPTION OF THE EMBODIMENTS

For further illustrating the invention, detailing experiments are described below. It should be noted that the following examples are intended to describe but not to limit the invention.

Example 1

The preparation of supported alloy catalysts: the metal salts of tin and iron, cobalt, nickel, rhodium, ruthenium, palladium, iridium and platinum were supported on a carrier by an incipient impregnation method. Water is used as the solvent to dissolve metal salts and the carrier is selected from activated carbon, alumina, silica, silicon carbide, zirconia, zinc oxide and titanium dioxide, or a mixture thereof. The catalyst was dried overnight at 120° C., and then reduced at 300° C. for 2 h. Finally, the catalyst should be passivated under 1% $O_2/N_2$ (V/V) for 4 h before use.

Example 2

The preparation of nickel supported on stannic oxide catalyst: 1.8 g $Ni(NO_3)_2.6H_2O$ were dissolved in 20 ml water, then 1.5 g $SnO_2$ was added to the prepared solution followed by stirring at 25° C. for 12 h until the complete evaporation of water. The catalyst was dried at 120° C. for 8 h, and then calcined at 300° C. for 2 h under $N_2$, and finally reduced at 300° C. for 2 h under $H_2$.

Example 3

The preparation of nickel supported on ferric oxide catalyst: 0.9 g $SnCl_4.5H_2O$ was dissolved in 20 ml water, then 1.5 g Fe$_2$O$_3$ was added to the prepared solution followed by stirring at 25° C. for 12 h until the complete evaporation of water. The catalyst was dried at 120° C. for 8 h, and then calcined at 300° C. for 2 h under N$_2$, and finally reduced at 300° C. for 2 h under H$_2$.

Example 4

The preparation of hydrogenation catalyst: platinum chloride, palladium chloride, ruthenium chloride, rhodium chloride, iridium chloride, nickel nitrate, ferric nitrate, cobalt nitrate and copper nitrate were dissolved in water, respectively. The prepared different metal salts solutions were impregnated on a carrier by an incipient impregnation method, respectively. The catalyst was dried at 120° C. overnight.

For the supported precious catalysts of platinum, palladium, ruthenium, rhodium, iridium, etc., the catalyst were reduced at 250° C. for 2 h, followed by passivated under 1% O$_2$/N$_2$ (V/V) for 4 h before use. For the supported non-precious catalysts of nickel, iron, cobalt, copper, etc., the catalyst were reduced at 450° C. for 2 h, followed by passivated under 1% O$_2$/N$_2$ (V/V) for 4 h before use.

Example 5

The in situ preparation of the alloy catalyst: The combination of metallic tin or tin compounds, or a mixture thereof and metallic hydrogenation catalyst or skeletal catalyst was put into the reactor. The reaction conditions are the same as Example 7, and the alloy catalyst is in situ formed.

Example 6

The preparation of skeletal alloy catalyst (hydrothermal treatment): 0.6 g metallic tin, 1.0 g skeletal nickel catalyst (Raney Ni) and 10-100 mL water were put into the kettle. The hydrothermal treatment was carried out under 7 MPa H$_2$ at 250° C. for 3 h. After the treatment, the obtained catalyst was dried overnight at 120° C. before use. FIG. 1 was the XRD spectra of the obtained NiSn alloy catalyst prepared by hydrothermal treatment. The XRD results showed that the formation of NiSn alloy after hydrothermal treatment.

Example 7

Catalytic conversion experiment: 0.25 g carbohydrate, a designed amount of composite catalyst and 25 ml water were put into the 75 ml autoclave. After flushing with hydrogen for three times, the reactor was pressurized with 5 MPa H$_2$, and then the temperature was increased to a designed temperature and kept for 30-240 min. After the reaction, the autoclave was cooled to room temperature. The liquid products were separated from catalysts by centrifugation. The liquid products were analyzed by high performance liquid chromatography, and only the yields of ethylene glycol, hexitol (sorbitol and mannitol) and 1,2-propylene glycol were calculated.

Example 8

Results of cellulose conversion to polyols over supported alloy catalysts. The alloy catalyst was composed of two components, in which one component was metallic tin and the other was transition metals. The loadings of metallic tin and transition metals were 3% and 5%, respectively. The reaction conditions are the same as Example 7.

TABLE 1

Results of cellulose conversion to polyols over supported alloy catalysts (supported alloy catalyst 0.1 g, reaction temperature 245° C., reaction time 95 min)

| Catalyst | Conversion of cellulose/% | Yield of ethylene glycol/% | Yield of 1,2-propylene glycol/%) | Yield of hexitol/% |
|---|---|---|---|---|
| Ni/AC | 100 | 7.3 | 6.6 | 29.4 |
| Ru/AC | 100 | 8.1 | 5.7 | 19.2 |
| Pt/AC | 98 | 5.6 | 5.3 | 22.9 |
| Ir/AC | 90 | 7.8 | 11.2 | 20.3 |
| NiSn/AC | 100 | 38.7 | 9.5 | 6.1 |
| RuSn/AC | 100 | 39.8 | 9.7 | 5.4 |
| PtSn/AC | 100 | 43.6 | 7.5 | 1.5 |
| IrSn/AC | 100 | 54.4 | 13.2 | 4.6. |
| Ni/SnO$_2$ | 100 | 45.6 | 10.1 | 5.2 |
| Sn/Fe$_2$O$_3$ | 100 | 26.8 | 11.9 | 6.1 |

As shown in Table 1, supported alloy catalysts promoted the production of ethylene glycol. Comparing the yields of ethylene glycol and hexitol over alloy catalysts and transition metals hydrogenation catalyst, the formation of alloy improved the yield of ethylene glycol, but the yield of hexitol decreased.

Example 9

Results of cellulose conversion to polyols over non-supported alloy catalyst. The alloy catalyst was composed of two components, in which one component was metallic tin and the other was transition metals. The reaction conditions are the same as Example 7.

TABLE 2

Results of cellulose conversion to polyols over non-supported alloy catalysts (non-supported alloy catalyst 0.05 g, the mass ratio of tin to nickel, copper and cobalt was 1:3, 1:5 and 1:2.5 respectively, reaction temperature 245° C., reaction time 95 min)

| Catalyst | Conversion of cellulose/% | Yield of ethylene glycol/% | Yield of 1,2-propylene glycol/% | Yield of hexitol/% |
|---|---|---|---|---|
| Raney Ni | 82 | 6.4 | 11.5 | 20.1 |
| Raney Cu | 85 | 4.3 | 9.6 | 27.9 |
| Raney Co | 76 | 5.8 | 4.5 | 18.9 |
| Raney NiSn | 100 | 54.5 | 13.3 | 4.6 |
| Raney CuSn | 100 | 56.9 | 10.3 | 5.9 |
| Raney CoSn | 100 | 50.2 | 11.3 | 6.1 |

As shown in Table 2, non-supported alloy catalysts promoted the production of ethylene glycol. Comparing the yields of ethylene glycol and hexitol over alloy catalysts and skeletal metals hydrogenation catalyst, the formation of alloy improved the yield of ethylene glycol, but the yield of hexitol decreased.

Example 10

Catalytic conversion results of different carbohydrates to polyols. RuSn/AC was used as supported alloy catalyst for the conversion of different carbohydrates. The mass ratio of tin to ruthenium was 1:3.5, and the loading of ruthenium was 5%. The reaction conditions are the same as Example 7.

TABLE 3

Results of catalytic conversion of different carbohydrates to polyols (RuSn/AC 0.1 g, reaction temperature 245° C., reaction time 95 min)

| Carbohydrate | Yield of ethylene glycol/% | Yield of 1,2-propylene glycol/% | Yield of glycerol/%) | Yield of sorbitol/% |
|---|---|---|---|---|
| cellulose | 58.7 | 9.5 | 1.8 | 6.1 |
| jerusalem artichoke | 11.3 | 24.0 | 3.5 | 4.8 |
| soluble starch | 27.0 | 19.7 | 6.4 | 16.8 |
| fructose | 17.3 | 24.2 | 25 | 0.8 |
| xylose | 49.4 | 20.9 | 12 | 1.5 |
| sucrose | 21.8 | 23.8 | 22 | 2.4 |
| glucose | 27.3 | 21.2 | 20 | 3.7 |
| sorbitol | 2.2 | 2.9 | 1.2 | 87.2 |
| xylitol | 2.5 | 2.4 | 1.0 | 92.5 (xylitol) |
| glycerol | 3.1 | 5.0 | 93 | — |

As shown in Table 3, RuSn/AC showed higher selectivity to ethylene glycol and 1,2-propylene glycol than sorbitol, which indicated that RuSn/AC was active for the C—C bond cleavage of carbohydrates bearing unsaturated bonds. The yield of ethylene glycol obtained from cellulose was higher than that form other carbohydrates. The selectivity of ethylene glycol and 1,2-propylene glycol depended on the carbohydrates. The yield of 1,2-propylene glycol would be improved, when the carbohydrates contained fructose or could be isomerized to fructose. However, RuSn/AC showed low activity towards the conversion of sorbitol, and C—C bonds of sorbitol could not be selectively cracked to produce ethylene glycol and 1,2-propylene glycol. Similarity, RuSn/AC showed low activity towards the conversion of xylitol and glycerol.

Example 11

Effect of reaction time. PtSn/AC (0.5% Sn, 5% Pt) was selected as supported alloy catalyst for the investigation of reaction time effect (Table 4). The reaction conditions are the same as Example 7 except for the reaction time.

TABLE 4

Results of catalytic conversion of cellulose to polyols at different time over PtSn/AC. (PtSn/AC 0.1 g, reaction temperature 245° C.)

| Time/min | Conversion of cellulose/% | Yield of ethylene glycol/% | Yield of 1,2-propylene glycol/%) | Yield of hexitol/% |
|---|---|---|---|---|
| 10 | 69 | 29.9 | 4.5 | 7.4 |
| 20 | 86 | 40.6 | 8.1 | 7.4 |
| 45 | 94 | 46.4 | 8.5 | 6.7 |
| 70 | 98 | 50.4 | 9.0 | 5.2 |
| 95 | 100 | 52.3 | 9.5 | 6.5 |
| 120 | 100 | 52.6 | 8.4 | 6.4 |
| 150 | 100 | 50.2 | 7.3 | 5.8 |

As shown in Table 4, PtSn/AC showed good activity towards the production of ethylene glycol in a certain period. The optimum reaction time was 1 h-2.5 h.

Example 12

Effect of reaction temperature. IrSn/AC (3.5% Sn, 5% Ir) was selected as supported alloy catalyst for the investigation of reaction temperature effect (Table 5). The reaction conditions are the same as Example 7 except for the reaction temperature.

TABLE 5

Results of catalytic conversion of cellulose to polyols at different temperature over IrSn/AC (IrSn/AC 0.2 g, reaction time 95 min)

| Temperature/° C. | Conversion of cellulose/% | Yield of ethylene glycol/% | Yield of 1,2-propylene glycol/% | Yield of hexitol/% |
|---|---|---|---|---|
| 215 | 48 | 18.7 | 2.3 | 11.7 |
| 225 | 67 | 34.1 | 2.8 | 7.2 |
| 235 | 90 | 52.3 | 9.5 | 5.7 |
| 245 | 100 | 64.7 | 9.5 | 6.1 |
| 255 | 100 | 50.5 | 9.3 | 3.8 |
| 265 | 100 | 46.8 | 6.8 | 1.6 |

As shown in Table 5, IrSn/AC showed good activity towards the production of ethylene glycol in a certain temperature range. The optimum reaction temperature was 230-260° C.

Example 13

The effect of mass ratio of Sn to Ir. IrSn/AC was selected as supported alloy catalyst for the investigation of mass ratio of Sn to Ir. The reaction conditions are the same as Example 7.

TABLE 6

The effect of mass ratio of Sn to Ir on the catalytic conversion of cellulose to polyols (IrSn/AC 0.1 g, reaction temperature 245° C., reaction time 95 min)

| Sn/Ir | Conversion of cellulose/%) | Yield of ethylene glycol/% | Yield of 1,2-propylene glycol/%) | Yield of hexitol/% |
|---|---|---|---|---|
| 3.2 | 100 | 46.4 | 10.2 | 5.1 |
| 1.8 | 100 | 53.6 | 9.2 | 4.9 |
| 1.2 | 100 | 58.6 | 9.5 | 6.5 |
| 0.6 | 100 | 51.6 | 6.3 | 8.9 |
| 0.3 | 100 | 40.3 | 7.8 | 11.2 |

As shown in Table 6, IrSn/AC showed good activity towards the production of ethylene glycol in a certain range of mass ratio of Sn to Ir. The optimum mass ratio was 0.6-1.8.

Example 14

The effect of LHSV. 5% Ir4% Sn/AC was selected as supported alloy catalyst for the investigation of the effect of LHSV. The reaction conditions are the same as Example 7.

TABLE 7

The effect of LHSV on the catalytic conversion of xylose to polyols (IrSn/AC 5 g, concentration of xylose aqueous solution 20 wt %, reaction temperature 245° C.)

| LHSV/h$^{-1}$ | Conversion of xylose/% | Yield of ethylene glycol/% | Yield of 1,2-propylene glycol/%) | Yield of hexitol/% |
|---|---|---|---|---|
| 0.2 | 100 | 36.4 | 11.2 | 6.1 |
| 0.5 | 100 | 41.6 | 14.5 | 4.9 |
| 0.8 | 100 | 45.7 | 18.2 | 3.2 |
| 1.1 | 100 | 39.2 | 13.4 | 7.9 |
| 1.7 | 100 | 31.3 | 7.8 | 11.2 |

As shown in Table 7, IrSn/AC showed good activity towards the production of ethylene glycol and 1,2-propylene glycol in a certain LHSV range. The optimum LHSV was 0.8 h$^{-1}$.

Example 15

The investigation and comparison of the stability of different alloy catalysts. Raney NiSn, 5% Ni3% Sn/AC and 5% Ir3% Sn/AC were selected as alloy catalysts for the investigation of catalysts stability. The reaction conditions are the same as Example 7.

TABLE 8

The investigation and comparison of the stability of alloy catalysts. (Raney Ni 0.08 g, NiSn/AC 0.1 g, reaction temperature 245° C., reaction time 95 min)

| Catalyst | Number of usage | Yield of ethylene glycol/% | Yield of 1,2-propylene glycol/% | Yield of hexitol/% |
|---|---|---|---|---|
| Raney NiSn | 1 | 60.4 | 13.2 | 4.6. |
| Raney NiSn | 2 | 59.8 | 10.9 | 4.2 |
| Raney NiSn | 3 | 54.9 | 11.1 | 5.8 |
| Raney NiSn | 4 | 53.7 | 13.6 | 2.9 |
| NiSn/AC | 1 | 38.7 | 9.5 | 6.1 |
| NiSn/AC | 2 | 28.5 | 8.2 | 5.4 |
| NiSn/AC | 3 | 20.3 | 6.5 | 4.5 |
| NiSn/AC | 4 | 14.4 | 4.2 | 3.1 |
| IrSn/AC | 1 | 54.4 | 13.2 | 4.6 |
| IrSn/AC | 2 | 52.3 | 13.0 | 4.0 |
| IrSn/AC | 4 | 50.1 | 12.0 | 4.7 |

As shown in Table 8, Raney NiSn showed good activity towards the production of ethylene glycol in the first four cycles. ICP analysis results of the aqueous solution after every recycle showed that the concentration of nickel and tin was lower than 1 ppm, which indicated that the leaching amount of active ingredient of Raney NiSn was few. IrSn/AC also showed good activity and stability in the conversion of cellulose to ethylene glycol. However, the catalytic activity and stability of NiSn/AC were worse than that of Raney NiSn. Skeletal NiSn alloy catalyst (Raney NiSn) showed superior catalytic activity.

The alloy catalyst in this invention could catalyze the highly efficient conversion of carbohydrates to ethylene glycol and 1,2-propylene glycol. The method in this invention possesses advantages of easy operation and low cost. Besides, the alloy catalysts provided by this method possess advantages of few leaching amount, good hydrothermal stability and easy to recycle.

We claim:

1. A method for catalytic conversion of carbohydrates to low-carbon diols, comprising: subjecting a carbohydrate feedstock to catalytic hydrogenation at an elevated pressure in water in the presence of an alloy catalyst,
wherein the alloy catalyst consists of tin and one or more transition metals selected from the group consisting of nickel, iron, cobalt, rhodium, ruthenium, palladium, iridium, copper, and a mixture thereof,
wherein a weight ratio between tin and the one or more transition metals is in a range of 0.01-100,
wherein the catalytic hydrogenation reaction is conducted in a reactor filled with hydrogen at a temperature higher than 120° C. for a reaction time no less than 5 minutes or at a liquid hourly space velocity of not more than 20 h$^{-1}$,
wherein a weight concentration of the alloy catalyst in the reaction system is between 0.1 wt % and 50 wt %, and
wherein the low-carbon diol comprises ethylene glycol and 1,2-propylene glycol, wherein a yield of ethylene glycol is higher than a yield of 1,2-propylene glycol, and wherein tin in the alloy is metallic.

2. The method of claim 1, wherein the hydrogen is filled in the reactor prior to the catalytic hydrogenation reaction, and an initial hydrogen pressure at room temperature is between 1 and 12 MPa, and the reaction temperature is lower than a thermal decomposition temperature of the low carbon diol.

3. The method of claim 1, wherein the reaction temperature is between 200° C. and 280° C. and the initial hydrogen pressure at room temperature is between 3 and 7 MPa.

4. The method of claim 1, wherein the alloy catalyst is a skeletal alloy catalyst composed of a nickel-tin alloy, the weight ratio between tin and nickel is in the range of 0.1-10, and the weight concentration of alloy catalyst in the reaction system is between 1 wt % and 30 wt %.

5. The method of claim 4, wherein the weight ratio between tin and nickel in the skeleton alloy catalyst is in the range of 0.5-2; the weight concentration of alloy catalyst in the reaction system is between 2 wt % and 20 wt %.

6. The method of claim 1, wherein the alloy catalyst is a supported catalyst, wherein metallic tin and the one or more transition metals are supported on a carrier, wherein the carrier is selected from the group consisting of activated carbon, alumina, silica, silicon carbide, zirconia, zinc oxide and titanium dioxide, and a mixture thereof, wherein a the weight concentration of alloy in the supported catalyst is between 0.01 wt % and 50 wt %, and wherein the weight ratio between tin and the one or more transition metals in the supported catalyst is in the range of 0.1-10.

7. The method of claim 6, wherein the weight concentration of alloy in the supported catalyst is between 1 wt % and 35 wt %, and wherein the weight ratio between tin and the one or more transition metals in the supported catalyst is in the range of 0.5-2.

8. The method of claim 1, wherein the carbohydrate feedstock comprises cellulose, starch, hemicellulose, glucose, mannose, xylose, arabinose, xylooligosaccharide, erythrose, chitosan, or a mixture thereof.

9. The method of claim 1, wherein the reaction time is between 0.5 h and 5 h in a sealed high pressure reactor.

10. The method of claim 1, wherein the reactor has a liquid hourly space velocity between 0.1 and 20 h$^{-1}$ in a semi continuous high pressure reactor or a continuous high pressure reactor, wherein the liquid hourly space velocity is a ratio of a total dry mass of the carbohydrate feedstock into the reactor per hour to a total mass of catalyst in the reactor.

11. The method of claim 1, wherein the alloy catalyst is converted from the precursor of the alloy catalyst in situ in the reactor, wherein the precursor of the alloy catalyst comprises a precursor of tin and a precursor of the one or more transition metals, wherein the precursor of tin is metallic tin, one or more tin compounds, or a mixture thereof, and the precursor of the one or more transition metals are selected from the group consisting of metallic and chemical compounds of nickel, iron, cobalt, rhodium, ruthenium, palladium, iridium, copper, and a mixture thereof.

12. The method of claim 11, wherein the precursor of the one or more transition metals is supported on a carrier, and the carrier is the precursor of tin, and wherein a weight concentration of transition metals in the catalyst is between 0.01 wt % and 50 wt %.

13. The method of claim 11, wherein the precursor of tin is supported on a carrier and the carrier is the precursor of the one or more transition metals, and the weight concentration of tin in the catalyst is between 0.01 wt % and 50 wt %.

14. The method of claim 11, wherein the precursor of tin is metallic tin, stannous fluoride, stannous fluoride, stannous bromide, stannous iodide, stannic fluoride, stannic chloride, stannic bromide, stannic iodide, stannic hydroxide, stannous hydroxide, stannous oxide, stannic oxide, stannous monosulphate, stannic acetate, stannous oxalate, sodium stannate, potassium stannate, calcium stannate, tin phosphide, stannous pyrophosphate, or a mixture thereof.

15. The method of claim 11, wherein the precursor of the one or more transition metals is metallic iron, metallic cobalt, metallic rhodium, metallic ruthenium, metallic palladium, metallic iridium, metallic copper, skeletal iron (Raney iron), skeletal cobalt (Raney cobalt), skeletal copper (Raney copper), ferric nitrate, cobalt nitrate, ruthenium nitrosyl nitrate, rhodium nitrate, palladium nitrate, iridium nitrate, copper nitrate, ferric chloride, cobalt chloride, ruthenium chloride, rhodium chloride, palladium chloride, iridium chloride, copper chloride, ferric oxide, ferroferric oxide, ferrous oxide, iron sulfate, cobalt(II) oxide, cobalt sesquioxide, cobaltosic oxide, cobaltous sulfate, nickel sulfate, copper oxide and copper sulfate, or a mixture thereof.

16. The method of claim 1, wherein the carbohydrate feedstock is cellulose, starch, hemicellulose, xylose, and/or glucose and a yield of ethylene glycol is higher than a yield of propylene glycol.

17. A method for catalytic conversion of carbohydrates to low-carbon diols, comprising: subjecting a carbohydrate feedstock to catalytic hydrogenation at an elevated pressure in water in the presence of an alloy catalyst,
wherein the alloy catalyst is a skeletal nickel-tin catalyst, a skeletal copper-tin catalyst, or a skeletal cobalt-tin catalyst, wherein a weight ratio between tin and the one or more transition metals is in a range of 0.01-100.
wherein the catalytic hydrogenation reaction is conducted in a reactor filled with hydrogen at a temperature higher than 120 ° C. for a reaction time no less than 5 minutes or at a liquid hourly space velocity of not more than 20 $h^{-1}$,
wherein a weight concentration of the alloy catalyst in the reaction system is between 0.1 wt % and 50 wt %, and
wherein the low-carbon diol comprises ethylene glycol and 1,2-propylene glycol, wherein a yield of ethylene glycol is higher than a yield of 1,2-propylene glycol, and wherein tin in the alloy is metallic.

18. The method of claim 17, wherein a total yield of ethylene glycol and 1,-propylene glycol is higher than 20%.

19. The method of claim 17, wherein the skeletal tin-nickel catalyst is prepared by hydrothermal reaction between metallic tin and skeletal nickel.

* * * * *